United States Patent [19]

Surabian

[11] Plant 4,566

[45] Jul. 8, 1980

[54] NECTARINE TREE

[75] Inventor: Aaron Surabian, Reedley, Calif.

[73] Assignee: Surabian Bros., Reedley, Calif.

[21] Appl. No.: 11,232

[22] Filed: Feb. 12, 1979

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Huebner & Worrel

[57] ABSTRACT

A new variety of nectarine tree discovered as a seedling of an open pollenated Red Grand nectarine tree growing in Fresno County, located in the San Joaquin Valley of California. The fruit of the new variety tends to ripen later than the Red Grand variety and is characterized by a strong red color over a moderate orange, the strong red coloring spreads from a substantially solid covering near the base of the fruit to blotches of strong red coloring near the apex.

1 Drawing Figure

BACKGROUND OF THE VARIETY

The newly discovered variety of nectarine tree is characterized by yellow-fleshed, clingstone fruit, and a tree similar in many respects to the Red Grand variety of nectarine tree, the subject of U.S. Plant Pat. No. 1,060, which ripens earlier than the new discovered variety.

ORIGIN AND ASEXUAL REPRODUCTION OF THE NEW VARIETY

Seeds selected from open pollenated Red Grand variety nectarine trees were planted in a plot at the southwest corner of Sumner and Buttonwillow Avenues near Reedley, Calif., located in the San Joaquin Valley. A seedling was selected and bud wood was taken therefrom. Several trees growing in a test plot for a commercial orchard located near Monson, in Fresno County, Calif., were grafted-over using bud wood taken from the selected seedling and the grafted-over trees have been carefully watched. Comparisons of fruit taken from the grafted-over trees and the seedling confirm that the new variety of nectarine tree is distinct by virtue of coloring of the fruit and dates of ripening, which dates tend to be later than that of the patented Red Grand variety.

SUMMARY OF THE VARIETY

The fruit of the new variety is generally uniform and colors during the later part of the first week in August and becomes fully ripe between the third and fourth weeks of August, when grown under conditions normally found in the San Joaquin Valley of California. The fruit of the new variety tends to ripen later than the Red Grand variety and is characterized by a strong red color over a moderate orange, the strong red coloring spreads from a substantially solid covering near the base of the fruit to blotches of strong red coloring near the apex. The fruit has a long harvest period and keeps well on the trees.

BRIEF DESCRIPTION OF THE DRAWING

The accompanying drawing illustrates typical specimens of the fruit and foliage of the new variety. Two specimens being shown in cross-section, with the seeds thereof being separately shown, and four other specimens being shown from different perspectives for illustrating size, form and coloring; the foliage is shown to illustrate typical leaf size and form.

DETAILED DESCRIPTION

The following is a detailed description of my new variety with color terminology being in accordance with the Nickerson Color Fan, obtainable from Munsell Color Company, Baltimore 2, Md., except in instances where terminology having generally accepted meaning is employed.

Parentage: Seedling grown from a seed of an open pollenated Red Grand variety of nectarine tree, U.S. Plant Pat. No. 1,060.

Propagation: Maintains its distinguishing characteristics through asexual reproduction.

Locality where grown and observed:

*Near.*—Reedley, County of Fresno, Calif.

TREE

Branches:

*Size.*—Medium.

*Surface.*—Smooth.

*Color.*—Strong yellow green 5 GY 6/8.

Leaves:

*Size.*—Medium to large.

*Length.*—7 inches.

*Width.*—1.4 to 1.8 inches.

*Shape.*—Lanceolate, acuminate tip.

*Color.*—5 GY 4/3 moderate olive green.

*Marginal form.*—Crenate.

*Glandular characteristics.*—Prominent, mostly reniform, usually two found on base of leaf and one to two found on stem.

*Petiole.*—0.5 inches in length and 0.1 inches in thickness.

Stem glands: Large and reniform, usually two found on the base and 0 to 3 found on stem.

Flower: Similar in size, shape, color and dates to the patented Red Grand variety of nectarine tree.

FRUIT

Maturity: Colors during the later part of the first week in August and becomes fully ripe between the third and fourth weeks of August.

Size and shape:

*Uniformity.*—Generally uniform, globose.

*Transverse diameter, in suture plane.*—2.2 inches.

*Transverse diameter, at right angles to suture plane.*—2.4 inches.

Form: Generally symmetrical.

*Suture.*—Generally shallow with slight depression beyond pistil point.

*Ventral surface.*—Rounded, slightly lipped.

*Stem cavity.*—Generally rounded with suture showing to one side.

*Base.*—Oblate.

*Apex.*—Indented.

*Pistil point.*—Slight depression beyond pistil point.

Skin:

*Thickness.*—Medium.

*Texture.*—Smooth.

*Tendency to crack.*—Slight to none.

*Color.*—Strong red 5 R 4/12 over moderate orange yellow 10 YR 8/10. The strong red color tends to comprise a solid covering near the base and changes to blotches of strong red coloring spreading over yellow near the apex of the fruit.

Flesh:

*Color.*—Brilliant yellow 5 Y 9/9.

*Pit well.*—Dark red, 2.5 R 3/9.

*Juice.*—Good.

*Flavor.*—Good, slightly tart.

*Aroma.*—Good.

*Texture.*—Meaty.

*Fibers.*—Few.

*Ripening.*—Generally evenly.

*Eating quality.*—Good.

Stone:

*Adherence to flesh.*—Tenacious, adheres to flesh.

*Fibers.*—Short and prominent.

*Size.*—Medium, average size 1.4 inches in length, 0.9 inches in width and 0.6 inches in thickness.

*Form.*—Generally elliptical, slightly oblique, having rounded sides.

*Hilum.*—Oval.

*Dorsal edge.*—Thin, prominent grooves extended from hilum to apex and of a length generally longer than the ventral edge.

*Ventral edge.*—Groove extended from hilum to apex, interrupted at midportion by grooves extended across the surface of the stone.

*Surface.*—Grooved and ridged toward apex end, and pitted toward base end, ridges generally are small and grooves generally are shallow.

*Color.*—Dark red, 2.5 R 3/7.

*Splitting tendency.*—None.

Use: Shipping.

Keeping quality: Very good.

Shipping quality: Very good.

Although the new variety of nectarine tree possesses the described characteristics as a result of the growing conditions in Fresno County, Calif., in the central portion of the San Joaquin Valley, it is to be understood that variations of the usual magnitude in characteristics incident to growing conditions, fertilization, pruning and pest control are to be expected.

Having thus described and illustrated my new variety of nectarine tree, what is new and desired to be secured by Letters Patent is:

1. A new and distinct variety of Nectarine tree, substantially as illustrated and described, which is similar in size, productivity and regularity of bearing to the Red Grand variety of nectarine tree from which the new variety was derived as a seedling, the seedling was grown from an open-pollenated seed taken from a tree of the Red Grand variety growing near an orchard containing trees of the late LeGrand variety of nectarine tree; the new variety bears generally uniform, clingstone fruit characterized by yellow flesh and smooth skin having a strong red coloring over a moderate orange coloring, the strong red coloring spreading from a substantially solid covering near the base of the fruit to blotches of a strong red coloring near the apex of the fruit, and the fruit ripens in the San Joaquin Valley of California about four weeks later than the fruit of the Red Grand variety.

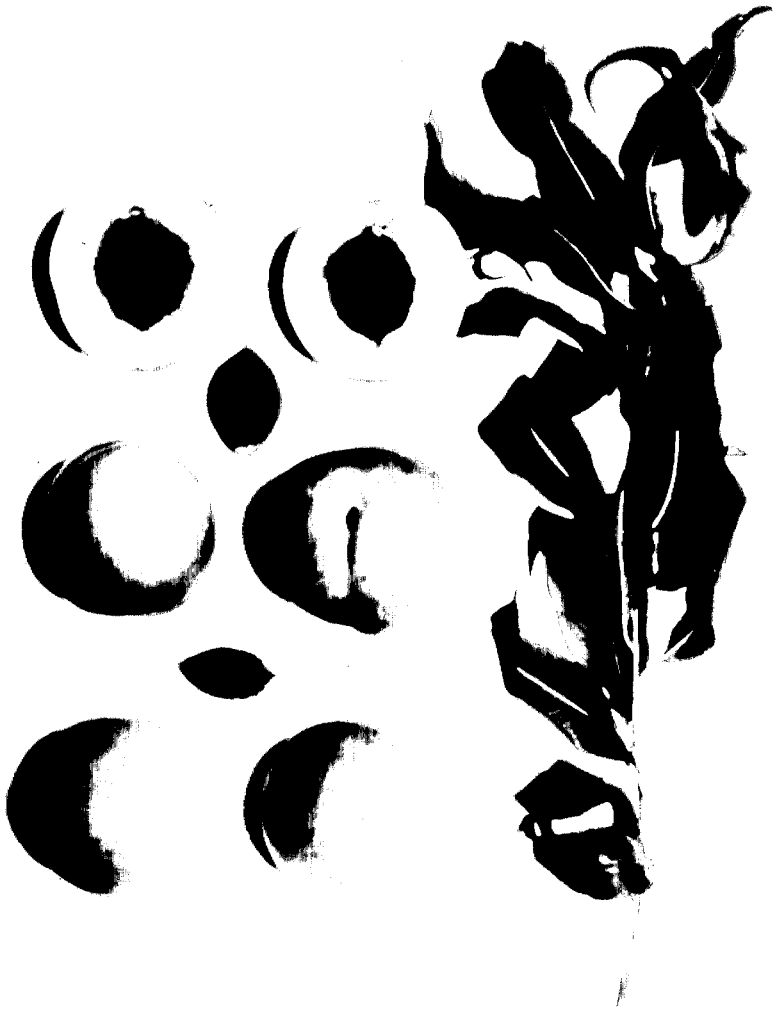

* * * * *